United States Patent
Hölscher et al.

(10) Patent No.: US 12,110,472 B2
(45) Date of Patent: Oct. 8, 2024

(54) PERFUMING INGREDIENTS WITH LILY OF THE VALLEY NOTE

(71) Applicant: SYMRISE AG, Holzminden (DE)

(72) Inventors: Bernd Hölscher, Halle (DE); Vijayanand Chandrasekaran, Holzminden (DE); Eva Ohrmann, Holzminden (DE)

(73) Assignee: SYMRISE AG, Holzminden (DE)

( * ) Notice: Subject to any disclaimer, the term of this patent is extended or adjusted under 35 U.S.C. 154(b) by 652 days.

(21) Appl. No.: 17/292,836

(22) PCT Filed: Nov. 13, 2018

(86) PCT No.: PCT/EP2018/081104
§ 371 (c)(1),
(2) Date: May 11, 2021

(87) PCT Pub. No.: WO2020/098923
PCT Pub. Date: May 22, 2020

(65) Prior Publication Data
US 2021/0395641 A1    Dec. 23, 2021

(51) Int. Cl.
| | |
|---|---|
| *C11B 9/00* | (2006.01) |
| *C07C 41/48* | (2006.01) |
| *C07C 45/51* | (2006.01) |
| *C07C 45/65* | (2006.01) |
| *C07C 67/31* | (2006.01) |
| *C07C 67/343* | (2006.01) |

(52) U.S. Cl.
CPC ............ *C11B 9/0034* (2013.01); *C07C 41/48* (2013.01); *C07C 45/515* (2013.01); *C07C 45/65* (2013.01); *C07C 67/31* (2013.01); *C07C 67/343* (2013.01); *C07C 2601/14* (2017.05); *C07C 2601/16* (2017.05)

(58) Field of Classification Search
None
See application file for complete search history.

(56) References Cited

U.S. PATENT DOCUMENTS

| 2010/0069287 A1 | 3/2010 | Fortineau |
| 2011/0117046 A1 | 5/2011 | Levorse, Jr. et al. |
| 2013/0090390 A1 | 4/2013 | Singer et al. |
| 2016/0108342 A1 | 4/2016 | Goeke et al. |

FOREIGN PATENT DOCUMENTS

| EP | 0251370 A1 | 1/1988 | |
| JP | H421649 A | 1/1992 | |
| JP | 2010508335 A | 3/2010 | |
| JP | 2016523827 A | 8/2016 | |
| WO | WO-2018167200 A1 * | 9/2018 | ........... C07C 47/225 |

OTHER PUBLICATIONS

International Search Report and Written Opinion issued on Apr. 14, 2019 for corresponding PCT Application No. PCT/EP2018/081104.
Michael J. Begley et al., "Topochemically controlled photodimerisation of crystalline methyl 6-isobutenyl-2-methyl-4-oxocyclohex-2-enecarboxylate: a chemical and X-ray crystallographic study," Journal of Chemical Society; 1979; pp. 976-989 XP002790381.
S. Murayama et al., "Synthesis of dl-tetrahydroeremophilone," Tetrahedron Letters; vol. 9, No. 34, 1968; pp. 3715-3717 XP002790382.
Japanese Office Action issued on Sep. 5, 2022 for corresponding JP Application No. 2021-525189.

* cited by examiner

*Primary Examiner* — Jessica Whiteley
(74) *Attorney, Agent, or Firm* — POLSINELLI PC

(57) ABSTRACT

The present invention primarily relates to the use of 3-(4-isobutyl-2-methyl-cyclohexyl)pro-panal, 3-(4-Isobutyl-6-methyl-cyclohexa-1,5-dien-1-yl)propanal, 3-(4-isobutyl-6-meth-ylene-cyclohexen-1-yl)propanal, or 3-(4-isobutyl-6-methyl-cyclohexen-1-yl)propanal as perfuming ingredients. Moreover, the present invention relates to perfume compositions and perfumed products comprising the before mentioned perfuming ingredients. Still more particularly, the invention relates to a method for producing said perfumed products and a method of imparting and/or increasing i) floral and/or ii) green and/or iii) lily of the valley odor characteristics to perfumed products. This invention also relates to 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, or 3-(4-isobutyl-6-methyl-cyclohexen-yl)propanal and a process for the preparation of said compounds.

20 Claims, No Drawings

PERFUMING INGREDIENTS WITH LILY OF THE VALLEY NOTE

CROSS-REFERENCE TO RELATED APPLICATIONS

This application is a national stage application (under 35 U.S.C. § 371) of PCT/EP2018/081104, filed Nov. 13, 2018, which is incorporated herein by reference in its entirety.)

The present invention primarily relates to the use of 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, or 3-(4-isobutyl-6-methyl-cyclohexen-1-yl)propanal as perfuming ingredients. Moreover, the present invention relates to perfume compositions and perfumed products comprising the before mentioned perfuming ingredients. Still more particularly, the invention relates to a method for producing said perfumed products and a method of imparting and/or increasing i) floral and/or ii) green and/or iii) lily of the valley odor characteristics to perfumed products. This invention also relates to 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, or 3-(4-isobutyl-6-methyl-cyclohexen-1-yl)propanal and a process for the preparation of said compounds.

Compounds with floral odor are an indispensable component in the perfume industry and in the production of cosmetics, body care products and washing and cleaning products. An especially valuable class of these floral fragrances are compounds with an odor note of lily of the valley.

Some representatives of this class of perfuming ingredients have a structure comprising a 4-alkyl-phenylpropanal as skeleton structure, for example 3-(4-tert-butylphenyl)-2-methylpropanal (other name: Lilial), 3-(4-tert-butylphenyl)propanal (other name: Bourgeonal), 3-(4-isopropylphenyl)-2-methylpropanal (Cyclamal), 3-(3-isopropylphenyl)-butanal (other name: Florhydral), and 3-(4-isobutyl-2-methylphenyl)propanal.

The use of 3-(4-isobutyl-2-methylphenyl)propanal as perfume ingredient is disclosed for example in WO2014/180945 A1.

3-(4-tert-Butylphenyl)-2-methylpropanal was for a long time one of the most important industrially used fragrances for floral fragrance compositions with an odor note of lily of the valley and was used in large quantities in the cosmetics and soaps industry. Then, however, results of animal tests showed that 3-(4-tert-butylphenyl)-2-methylpropanal could be reprotoxic. In addition, it was found that this compound is possibly an allergen and might cause contact dermatitis in sensitive persons.

It has been shown that 3-(4-tert-Butylphenyl)-2-methylpropanal enzymatically degraded in rats and dogs to tert-butyl benzoic acid (t-BBA), which is known to inhibit glucose synthesis and fatty acid synthesis in vitro (McCune et al, Arch Biochem Biophys (1982) 214 (1): 124-133). tert-Butyl benzoic acid is also known to cause testicular effects in male rats (Hunter et al. Food Cosmet. Toxicol. 1965, 3: 289-298; Cagen et al. J. Am. Coll. Toxicol. 1989, 8 (5): 1027-1038).

Despite the large number of perfuming ingredients already available, in the perfume industry there is still a general demand for new perfuming ingredients with a floral, especially lily of the valley odor note.

The primary problem to be solved by the present invention was to provide a perfuming ingredient with a floral, especially lily of the valley odor note. The perfuming ingredient should impart an odor impression that largely corresponds to the complexity of the natural odor of lily of the valley blossom.

These perfuming ingredients thereby preferably ought to meet one, several or preferably all of the following requirements:
easy access,
high efficacy at low concentration, preferably with an inherent odor that is not or hardly detectable at low concentrations,
complete colourlessness or colourlessness to a large extent,
high stability in various mixtures or preparations, wherein in particular no discolouration and/or separation and/or turbidity shall occur,
inert behaviour,
no toxic and/or allergenic effect towards humans.

Furthermore, with the present invention particularly novel, advantageous perfume composition, that contain such perfuming ingredients, shall be provided. Such perfume compositions preferably shall be suitable to fragrance or perfume certain products.

Moreover, perfumed products accordingly as well as methods for producing such products shall be provided.

The primary object of the present invention is solved by the use of a compound selected from the group consisting of 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, and 3-(4-isobutyl-6-methyl-cyclohexen-1-yl)propanal as a perfuming ingredient.

It was found, surprisingly, that 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, and 3-(4-isobutyl-6-methyl-cyclohexen-1-yl)propanal impart an odor impression that comes very close to the complexity of the natural odor of lily of the valley blossom. That is, the odor impression imparted by these compounds is characterized by outstanding naturalness and complexity, especially with respect to the odor note of lily of the valley. Such a complex odor impression, largely corresponding to the natural odor of lily of the valley blossom, has not previously been achieved with the fragrances with an odor note of lily of the valley known from the prior art.

The search for suitable substances with an odor note of lily of the valley, which led to the present invention, was hampered by the following circumstances:
the mechanisms of odor perception are not adequately known;
the relationships between special odor perception on the one hand and the chemical structure of the associated fragrance on the other hand have not been investigated sufficiently and ability to predict odor properties of molecules is not given;
even slight changes in the structural makeup of a known fragrance often bring about large changes in the sensory properties and impair compatibility of the compound for the human body.

The success of a search for suitable fragrances is therefore highly dependent on the intuition of the person conducting the search.

Further, no evidence was found that 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, or 3-(4-isobutyl-6-methylcyclohexen-1-yl)propanal is toxic to and/or shows an allergenic effect towards humans. Because this compounds are not aromatic (from the perspective of organic chemistry) an enzymatically degradation to tert-butyl benzoic acid (t-BBA) or other benzoic acids is not possible.

Further aspects of the invention can be seen from the following description, the practical examples, the figure and the appended patent claims.

A perfuming ingredient is, in the context of the present text, any substance that is suitable for being used for bringing about an olfactory impression, i.e. for imparting an olfactory impression, or for altering (modifying or intensifying) the olfactory perception of another substance.

3-(4-Isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, and 3-(4-isobutyl-6-methyl-cyclohexen-1-yl)propanal are compounds of the general formula (I)

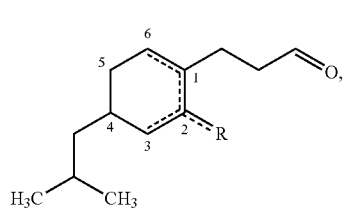

(I)

wherein
  a) all dashed bonds represent single bonds and R is $CH_3$ (3-(4-isobutyl-2-methyl-cyclohexyl)propanal),
  b) the dashed bonds between C1 and C6 and between C2 and C3 are double bonds and the remaining dashed bonds represent single bonds and R is $CH_3$ (3-(4-Isobutyl-6-methyl-cyclohexa-1,5-dien-1-yl)propanal),
  c) the dashed bonds between C1 and C6 and between C2 and R are double bonds and the remaining dashed bonds represent single bonds and R is $CH_2$ (3-(4-isobutyl-6-methylene-cyclohexen-1-yl)propanal),
or
  d) the dashed bond between C1 and C2 is a double bond and the remaining dashed bonds represent single bonds and R is $CH_3$ (3-(4-isobutyl-6-methyl-cyclohexen-1-yl) propanal). As can be seen from the general formula (I), all these compounds share a significant structural element and belong to the same class of chemical compounds.

3-(4-Isobutyl-2-methyl-cyclohexyl)propanal is a compound of the following formula (A):

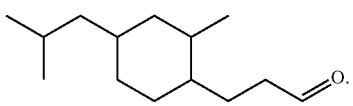

(A)

3-(4-Isobutyl-2-methyl-cyclohexyl)propanal is another aspect of the present invention. 3-(4-Isobutyl-2-methyl-cyclohexyl)propanal has three stereocenters, giving it eight possible stereoisomers (A1 to A9) which are shown below. 3-(4-Isobutyl-2-methyl-cyclohexyl)propanal can be used as a mixture of all or several stereoisomers (A1 to A9) or the stereoisormers A1 to A9 can be used independently.

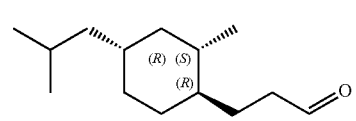

(A1)

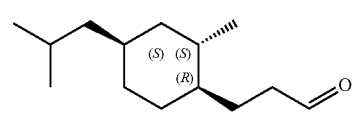

(A2)

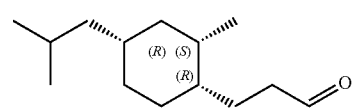

(A3)

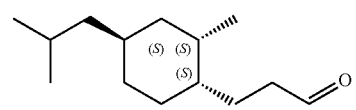

(A4)

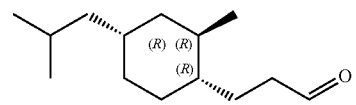

(A5)

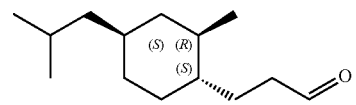

(A6)

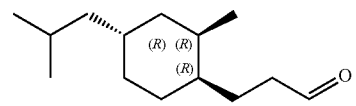

(A7)

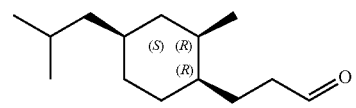

(A8)

3-(4-Isobutyl-6-methyl-cyclohexa-1,5-dien-1-yl)propanal is a compound of the following formula (B):

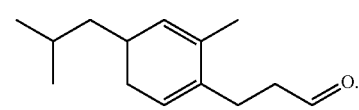

(B)

3-(4-Isobutyl-6-methyl-cyclohexa-1,5-dien-1-yl)propanal is another aspect of the present invention. 3-(4-Isobutyl-6-methyl-cyclohexa-1,5-dien-1-yl)propanal has one stereocenter, giving it two possible enantiomers (B1 to B2) which are shown below. 3-(4-Isobutyl-6-methyl-cyclohexa-1,5-dien-1-yl)propanal can be uses as a racemic mixture or as a mixture of both enantiomers.

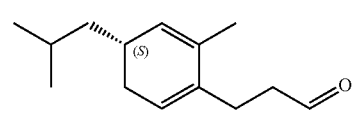

(B1)

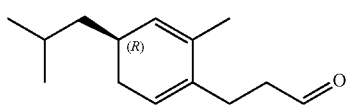

(B2)

3-(4-Isobutyl-6-methylene-cyclohexen-1-yl)propanal is a compound of the following formula (C):

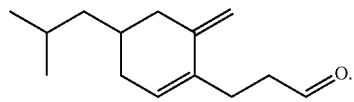

(C)

3-(4-Isobutyl-6-methylene-cyclohexen-1-yl)propanal is another aspect of the present invention. 3-(4-Isobutyl-6-methylene-cyclohexen-1-yl)propanal has one stereocenter, giving it two possible enantiomers (C1 and C2) which are shown below. 3-(4-Isobutyl-6-methylene-cyclohexen-1-yl)propanal can be uses as a racemic mixture or as a mixture of both enantiomers.

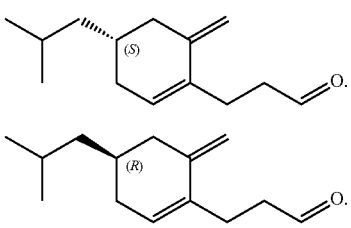

(C1)

(C2)

3-(4-Isobutyl-6-methyl-cyclohexen-1-yl)propanal is a compound of the following formula (D):

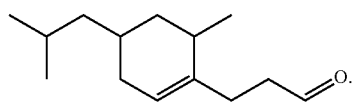

(D)

3-(4-Isobutyl-6-methyl-cyclohexen-1-yl)propanal is another aspect of the present invention. 3-(4-Isobutyl-6-methyl-cyclohexen-1-yl)propanal has two stereocenter, giving it four possible stereoisomers (D1 to D4) (diastereomers) which are shown below. 3-(4-Isobutyl-6-methyl-cyclohexen-1-yl)propanal can be used as a mixture of all or several stereoisomers (D1 to D4).

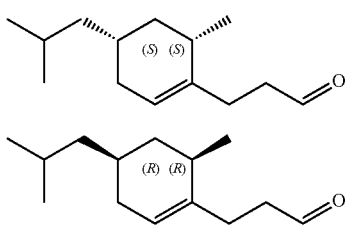

(D1)

(D2)

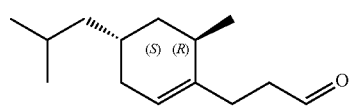

(D3)

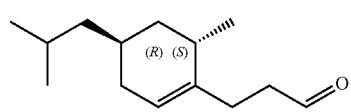

(D4)

The present invention also relates to a compound selected from the group consisting of 3-(4-Isobutyl-2-methyl-cyclohexyl)propanal, 3-(4-Isobutyl-6-methyl-cyclohexa-1,5-dien-1-yl)propanal, 3-(4-Isobutyl-6-methylene-cyclohexen-1-yl)propanal, and 3-(4-Isobutyl-6-methyl-cyclohexen-1-yl) propanal.

The use according to the invention is preferred, wherein the perfuming ingredient has i) floral and/or ii) green and/or iii) lily of the valley odor characteristics. The use according to the invention is, wherein the perfuming ingredient has further sweet or creamy odor characteristics.

In accordance with the foregoing, another aspect of the invention relates in particular to a perfume composition comprising at least one compound selected from the group consisting of 3-(4-isobutyl-2-methyl-cyclohexyl)propanal, 3-(4-Isobutyl-6-methyl-cyclohexa-1,5-dien-1-yl)propanal, 3-(4-isobutyl-6-methylene-cyclohexen-1-yl)propanal, and 3-(4-isobutyl-6-methyl-cyclohexen-1-yl)propanal.

Perfume compositions according to the invention are usually liquid at 25° C. and 1013 hPa and normally are homogeneous solutions.

Perfume compositions often comprise synthetic or natural (preferably) taste and odor neutral carrier oils, which contain the scent or fragrance substance (as artificial or natural substances) in highly concentrated form (as well as perfumistic solvents and/or auxiliary materials, if applicable). The same applies accordingly to the perfume compositions according to the invention described herein.

Preferably, the perfume composition according to the invention comprises one or more additional fragrance ingredients.

Examples for fragrance ingredients that generally preferably can be used as component of a perfume composition according to the invention can be found for example in S. Arctander, Perfume and Flavor Chemicals, Vol. I and II, Montclair, N.J., 1969, author's edition or H. Surburg, J. Panten, Common Fragrance and Flavor Materials, 5th Ed., Wiley-VCH, Weinheim 2006.

Preferred ethereal oils, concretes, absolutes, resins, resinoids, balsams and/or tinctures, that can be a fragrance ingredient of a perfume composition according to the invention are preferably to be selected from the group consisting of:

Ambergris tincture; amyris oil; *angelica* seed oil; *angelica* root oil; aniseed oil; valerian oil; basil oil; tree moss absolute; bay oil; mugwort oil; benzoin resin; bergamot oil; beeswax absolute; birch tee oil; bitter almond oil; savory oil; bucco leaf oil; cabreuva oil; cade oil; calmus oil; camphor oil; *cananga* oil; cardamom oil; cascarilla oil; *cassia* oil; cassie absolute; castoreum absolute; cedar leaf oil; cedar wood oil; cistus oil; citronella oil; citrus oil; copaiva balsam; copaiva balsam oil; coriander oil; costus root oil; cumin oil; cypress oil; davana oil; dill weed oil; dill seed oil; eau de brouts absolute; oakmoss absolute; elemi oil; estragon oil; *eucalyptus citriodora* oil; *eucalyptus* oil;

fennel oil; spruce needle oil; *galbanum* oil; *galbanum* resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; chamomile oil blue; chamomile oil roman; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil squeezed; linaloe oil; *litsea cubeba* oil; bay leaf oil; macis oil; Marjoram oil; mandarin oil; *massoia* bark oil; *mimosa* absolute; musk seed oil; musk tincture; muscatel sage oil; nutmeg oil; myrrh absolute; myrrh oil; myrtle oil; carnation leaf oil; carnation blossom oil; neroli oil; olibanum absolute; olibanum oil; opopanax oil; orange blossom absolute; orange oil; *origanum* oil; palmarosa oil; patchouli oil; *perilla* oil; peru balsam oil; parsley leaf oil; parsley seed oil; petitgrain oil; peppermint oil; pepper oil; allspice oil; pine oil; poley oil; rose absolute; rosewood oil; rose oil; rosemary oil; sage oil Dalmatian; sage oil Spanish; sandalwood oil; celery seed oil; spike lavender oil; star aniseed oil; *styrax* oil; *tagetes* oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; vermouth oil; wintergreen oil; ylang oil; ysop oil; civet absolute; cinnamon leaf oil; cinnamon bark oil.

Preferred single fragrance substances that can be preferably used as fragrance ingredients of a perfume composition according to the invention are selected from the group of hydrocarbons, thereby preferred 3-carene; a-pinene; b-pinene; a-terpinenes; g-terpinenes; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, thereby preferred hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and their acetals, thereby preferred hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyl oxyacetaldehyde; 1-(1-methoxypropoxy)-(E/Z)-3-hexene;

aliphatic ketones and their oximes, thereby preferred 2-heptanone; 2-octanone; 3-octanone; 2-nonanone; 5-methyl-3-heptanone; 5-methyl-3-heptanone oxime; 2,4,4,7-tetramethyl-6-octene-3-one; 6-methyl-5-heptene-2-one;

aliphatic sulphur-containing compounds, thereby preferred 3-methylthio-hexanol; 3-methyl-thiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles, thereby preferred 2-nonenoic acid nitrile; 2-undecenoic acid nitrile; 2-tridecenoic acid nitril; 3,12-tridecadienoic acid nitrile; 3,7-dimethyl-2,6-octadienoic acid nitrile; 3,7-dimethyl-6-octenoic acid nitril;

esters of aliphatic carboxylic acids, thereby preferred (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate; 4-methyl-2-pentyl-crotonate;

acyclic terpene alcohols, thereby preferred citronellol; geraniol; Nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as their formates, acetates, propionates, isobutyrates, butyrates, isovalerianates, pentanoates, hexanoates, crotonates, tiglinates and 3-methyl-2-butenoates;

acyclic terpene aldehydes and -ketones, thereby preferred geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl acetals of geranial, neral, 7-hydroxy-3,7-dimethyloctanal;

cyclic terpene alcohols, thereby preferred isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; as well as their formates, acetates, propionates, isobutyrates, butyrates, isovalerianates, pentanoates, hexanoates, crotonates, tiglinates and 3-methyl-2-butenoates; menthyl formate; menthyl propionate; menthyl butyrate; menthyl isobutyrate; menthyl isovalerianate; menthyl hexanoate; menthyl crotonate; menthyl tiglinate;

cyclic terpene aldehydes and -ketones, thereby preferred menthone; isomenthone; 8-mercaptomenthan-3-one; carvone; camphor; fenchone; alpha-ionone; beta-ionone; beta-n-methyl ionone; beta-isomethyl ionone; alpha-irone; alpha-damascone; beta-damascone; beta-damascenone; delta-damascon; gamma-damascon; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methyl cedryl ketone);

cyclic alcohols, thereby preferred 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, thereby preferred alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, thereby preferred cineol; cedryl methyl ether; cyclododecyl methyl ether; 1,1-dimethoxycyclododecane; (ethoxymethoxy)cyclododecane; alphacedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones, thereby preferred 4-tert.-butyl cyclohexanone; 2,2,5-trimethyl-5-pentyl cyclopentanone; 2-heptyl cyclopentanone; 2-pentyl cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes, thereby preferred 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, thereby preferred 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethyl-ketone; methyl-2,6,10-trimethyl-2,5,9-cyclododecatrienylketone; tert.-butyl-(2,4-dimethyl-3-cyclohexen-1-yl)ketone;

esters of cyclic alcohols, thereby preferred 2-tert-butyl-cyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

esters of cycloaliphatic alcohols, preferably 1-cyclohexylethyl crotonate;

esters of cycloaliphatic carboxylic acids, thereby preferred allyl-3-cyclohexyl propionate; allyl cyclohexyloxy acetate; cis- and trans-methyldihydrojasmonate; cis- and trans-methyljasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

araliphatic alcohols, thereby preferred benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentan-1-ol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, thereby preferred benzyl acetate; benzyl propionate; benzyl isobutyrate; benzyl isovalerianate; 2-phenylethyl acetate; 2-phenylethyl propionate; 2-phenylethyl isobutyrate; 2-phenylethyl isovalerianate; 1-phenylethyl acetate; alpha-trichloromethyl benzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, thereby preferred 2-phenylethyl methyl ether; 2-phenylethyl isoamyl ether; 2-phenylethyl-1-ethoxyethyl ether; phenyl acetaldehyde dimethyl acetal; phenyl acetaldehyde diethyl acetal; hydratropic aldehyde dimethyl acetal; phenyl acetaldehyde glyceryl acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

aromatic and araliphatic aldehydes, thereby preferred benzaldehyde; phenyl acetaldehyde; 3-Phenyl propanal; hydratropic aldehyde; 4-methyl benzaldehyde; 4-methylphenyl acetaldehyde; 3-(4-ethylphenyl)-2,2-dimethyl propanal; 2-methyl-3-(4-isopropylphenyl)propanal; 2-methyl-3-(4-tert.-butylphenyl)propanal; 2-methyl-3-(4-isobutylphenyl)propanal; 3-(4-tert.butylphenyl)propanal; cinnamic aldehyde; alpha-butyl cinnamic aldehyde; alpha-amyl cinnamic aldehyde; alpha-hexyl cinnamic aldehyde; 3-methyl-5-phenylpentanal; 4-methoxy benzaldehyde; 4-hydroxy-3-ethoxy benzaldehyde; 3,4-methylendioxy benzaldehyde; 3,4-dimethoxy benzaldehyde; 2-methyl-3-(4-methoxyphenyl)propanal; 2-methyl-3-(4-methylendioxyphenyl)propanal;

aromatic and araliphatic ketones, thereby preferred acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanylmethylketone; 6-tert.-butyl-1,1-dimethyl-4-indanylmethylketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and their esters, thereby preferred benzoic acid; Phenylacetic acid; methyl benzoate; ethyl benzoate; hexyl benzoate; methyl phenylacetate; ethyl phenylacetate; geranyl phenylacetate; phenylethyl-phenyl acetate; methyl cinnamate; ethyl cinnamate; benzyl cinnamate; phenylethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethyl benzoate; ethyl-3-phenylglycidate; ethyl-3-methyl-3-phenylglycidate;

nitrogen-containing aromatic compounds, thereby preferred 2,4,6-trinitro-1,3-dimethyl-5-tert.-butylbenzene; 3,5-dinitro-2,6-dimethyl-4-tert.-butyl acetophenone; cinnamic acid nitrile; 3-methyl-5-phenyl-2-pentenoic acid nitrile; 3-methyl-5-phenylpentanoic acid nitrile; methyl anthranilate; methy-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropyl chinolin; 6-isobutyl chinolin; 6-sec.-butyl chinolin; 2-(3-phenylpropyl)pyridine; indole; skatole; 2-methoxy-3-isopropyl pyrazine; 2-isobutyl-3-methoxy pyrazine;

phenols, phenyl ethers and phenyl esters, thereby preferred estragol; anethol; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds, thereby preferred 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, thereby preferred 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1, 15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,13-tridecandioate; coumarin; 2,3-dihydrocoumarin; octahydrocoumarin.

Accordingly, another aspect of the present invention relates to a perfumed product. A perfumed product according to the invention comprises at least one compound selected from the group consisting of 3-(4-isobutyl-2-methyl-cyclohexyl)propanal, 3-(4-Isobutyl-6-methylcyclohexa-1,5-dien-1-yl)propanal, 3-(4-isobutyl-6-methylene-cyclohexen-1-yl)propanal, and 3-(4-isobutyl-6-methyl-cyclohexen-1-yl)propanal, preferably in a sensorially effective amount.

Preferred perfumed products according to the invention are detergents and cleaning products, hygiene or care products, especially products from the area of body and hair care, cosmetics and household products.

Preferred products are for example perfume extraits, eau de parfums, eau de toilettes, aftershaves, eau de colognes, pre-shave products, splash colognes and perfumed refreshing tissues as well as perfumed or to be perfumed acidic, alkaline and neutral detergents, such as e.g. floor cleaners, window glass cleaners, dishwashing detergents, bathroom and sanitary cleaners, scouring agent, solid or liquid toilet cleaners, toilet sticks, toilet stones (liquid or solid), powdery or foamy carpet cleaners, liquid detergents, powdery detergents, laundry pretreatment agents such as bleaches, soaking agents and stain removers, fabric softeners, laundry soaps, laundry tablets, disinfectants, surface disinfectants as well as air improvers in liquid or gel-like form or applied to a solid carrier, particularly for deodorization of exhaust air from air conditioning and industrial processes, as well as air improvers in the form of aerosol or pump sprays, waxes and polishes such as furniture polishes, floor waxes, shoe creams, strengthening, impregnating or deodorizing textile treatment agents, diapers, sanitary towels, panty liners, plasters, as well as personal care agents such as e.g. solid and liquid soaps, shower gels, shampoos, shaving soap, shaving foams, bathing oils, damp cleaning cloths, cosmetic emulsion of the oil-in-water, water-in-oil and water-in-oil-in-water type such as e.g. skin creams and lotions, face creams and lotions, sun protection creams and lotions, after sun creams and lotions, hand creams and lotions, foot creams and lotions, depilatory creams and lotions, aftershave creams and lotions, tanning creams and lotions, hair care products such as e.g. hair sprays, hair gels, strengthening hair lotions, hair conditioners, permanent or semi-permanent hair dyes, hair forming agents such as cold waves and hair smoothing agents, hair tonics, hair creams and lotions, deodorants and antiperspirants such as e.g. armpit sprays, roll-ons, deo sticks, deo creams, products for decorative cosmetic such as e.g. eyeshadow, makeups, lipsticks, mascara as well as candles, lamp oils, incense sticks, animal litter, cat litter, insecticides, repellents, liquid and gaseous fuels, heating oils and heating gases.

Particularly preferred perfumed products according to the invention are selected from the group consisting of perfume extraits, eau de perfumes, eau de toilettes, aftershaves, eau de colognes, pre-shave products, splash colognes, perfumed refreshing tissues, acidic, alkaline and neutral detergents, textile fresheners, ironing aids, liquid detergents, powdery detergents, laundry pretreatment agents, fabric softeners, laundry soaps, laundry tablets, disinfectants, surface disinfectants, air improvers, aerosol sprays, waxes and polishes, personal care agents, hand creams and lotions, foot creams and lotions, depilatory creams and lotions, aftershave creams and lotions, tanning creams and lotions, hair care products, deodorants and antiperspirants, products for decorative cosmetic, candles, lamp oils, incense sticks, insecticides, repellents and fuels.

For purposes of clarification it has to be mentioned that (perfumed) products according to the invention within the scope of the present text are to be understood as products that have been caused or produced on purpose, but not as naturally occurring substance mixtures, for example such as the ones that can be obtained from plant-based starting materials by means of extraction.

The compounds according to the present invention are preferably a constituent of a perfume composition according to the invention. Therefore, in a preferred embodiment, a perfumed product comprises a perfume composition according to the invention, and a carrier or a substrate, wherein the carrier or the substrate is in direct contact with said perfume composition. The substrate is for example a solid substrate or the carrier is for example a solid carrier. The carrier or substrate guarantees a fine distribution of the perfume composition inside the product as well as a controlled release during application. Such carriers may be porous inorganic materials such as silica gels, zeolites, gypsums, clay, clay granules, aerated concrete etc. or organic materials such as woods and cellulose-based substances.

The compounds according to the present invention to be used according to the invention or perfume compositions according to the present invention may also be present in microencapsulated or spray-dried form, as inclusion complexes or as extrusion products and can be added to a product in this form.

If applicable, the properties of compounds according to the present invention to be used according to the invention or of perfume compositions according to the present invention can be further optimized by means of so-called "coating" with suitable materials with regard to a more targeted release, wherein preferably wax-like plastic materials such as e.g. polyvinyl alcohol are used.

A microencapsulation of the compounds according to the present invention to be used according to the invention or perfume compositions according to the present invention can take place, for example, by means of the so-called coacervation process with the aid of capsule materials, e.g. of polyurethane-like substances or soft gelatin. Spray-dried compounds according to the present invention can be produced, for example, by means of spray-drying of a compound according to the invention, i.e. of an emulsion or dispersion containing a compound according to the present invention or a perfume compositions according to the present invention, wherein modified starches, proteins, dextrins and/or plant-based gums can be used as carrier substance. Inclusion complexes can be produced, for example, by means of addition of dispersions, which are or comprise a compound according to the present invention or a perfume compositions according to the present invention, and cyclodextrins or urea derivatives into a suitable solvent, e.g. water. Extrusion products can take place by means of fusion of a compound according to the present invention or a perfume compositions according to the present invention with a suitable wax-like substance and extrusion with subsequent solidification, in a suitable solvent, e.g. isopropanol, if applicable.

The compounds according to the present invention or perfume compositions according to the present invention can be used in many preparations or products, wherein they are preferably combined with one or several of the following excipients or active ingredients:

Preserving agents, abrasives, anti-acne agents, agents against skin aging, antibacterial agents, anticellulite agents, antidandruff agents, anti-inflammatory agents, irritation preventing agents, irritation inhibiting agents, antimicrobial agents, antioxidants, astringents, sweat inhibiting agents, antiseptic agents, antistatic agents, binders, buffers, carrier materials, chelate builders, cell stimulants, cleaning agents, caring agents, depilatory agents, surface active agents, deodorizing agents, antiperspirants, plasticizers, emulsifiers, enzymes, ethereal oils, fibres, fixators, foam builders, foam stabilizers, substances to prevent foaming, foam boosters, fungicides, gelatinizing agents, gelforming agents, hair care products, hair forming products, smoothing agents, moisturizing agents, dampening substances, moist-keeping substances, bleaching agents, (textile-)strengthening agents, stain removing agents, optical brightening agents, impregnating agents, dirt-repellent agents, friction-lowering agents, lubricants, moisturizing creams, ointments, opacifiers, plasticizing agents, covering agents, polish, glazing agents, polymers, powders, proteins, regreasing substances, abrasive agents, silicones, skin soothing agents, skin cleaning agents, skin caring agents, skin healing agents, skin lightening agents, skin protecting agents, skin softening agents, cooling agents, skin cooling agents, warming agents, skin warming agents, stabilizers, UV-absorbing agents, UV-filters, detergents, fabric softeners, suspending agents, skin tanning agents, thickening agents, vitamins, oils, waxes, fats, phospholipids, saturated fatty acids, mono- or polyunsaturated fatty acids, α-hydroxy acids, polyhydroxy fatty acids, liquefying agents, dyes, color-protecting agents, pigments, anticorrosives, aromas, flavorings, aromatic substances, polyols, surfactants, electrolytes, organic solvents or silicon derivatives.

According to one embodiment of the present invention a preferred product according to the invention, particularly a deodorant or the like, additionally contains (depending on the desired mode of action) one or several of the following active substances:

(1) antimicrobially active substances that inhibit the development of microorganisms that are responsible for the smell of perspiration; for example Triclosanâ (5-chloro-2-(2,4-dichlorophenoxy)phenol), triclocarban, chlorhexidine, chlorhexidine hydrochloride, chlorhexidine diacetate, chlorhexidine digluconate, 2-phenoxyethanol, farnesol, glycerin esters and -ethers such as glyceryl monolaurate, glyceryl monocaprinate, hexoxyglycerin, octoxyglycerin (=ethylhexylglycerin, 3-(2-ethylhexyloxy-1,2-propanediol) or Sensiva® SC 50 (by Schülke & Mayr), aliphatic 1,2-diols such as e.g. 1,2-decanediol (EP 1 269 983), araliphatic alcohols such as for example described in EP 799 174, preferably 4-methyl-4-phenyl-2-pentanol (Vetikol; WO 03/024907) or 2-methyl-4-phenyl-2-butanol (1,1-dimethyl-3-phenylpropanol, alpha,alpha-dimethylphenethylcarbinol), 1-menthyl methyl ether as described in WO 02/41861, 2-benzylheptan-1-ol (Jasmol; 2-n-pentyl-3-phenylpropan-1-ol), 2,2-dimethyl-3-phenylpropanol (muguet alcohol; cf. U.S. Pat. No. 4,091,090), antimicrobially active secondary alcohols, such as for example described in WO 2005/004601, particularly 3-methyl-6-phenyl-2-hexanol, 4-(2,4-dimethylphenyl)-2-butanol, 6-(4-isopropylphenyl)-3-methyl-2-hexanol, 4-(2,4,5-trimethylphenyl)-2-butanol, 3,3-dimethyl-4-phenyl-2-butanol, 3-methyl-4-(2-methylphenyl)-2-butanol, 6-(3,4-dimethylphenyl)-2-hexanol, aliphatic carboxylic acids such as 2-hexyloctanoic acid, 2-hexyldecanoic acid, 2-butyloctanoic acid or 2-butyldecanoic acid;

(2) enzyme inhibiting substances that inhibit the effect of enzymes that participate in the formation of smell of perspiration; for example, citric acid esters and metal-chelating substances such as EDTA (ethylenediaminetetraacetic acid), EGTA [ethylenebis(oxyethylenenitrilo)-tetraacetic acid] and DTPA (diethylenetriaminepentaacetic acid, pentetic acid);

(3) odor absorbing substances that absorb substances that are responsible for the smell of perspiration; for example, zinc rizinoleate, cyclodextrins:

(4) antiperspirants that inhibit sweat secretion and thus eliminate the breeding grounds of bacteria that are responsible for body odor. Astringent metal salts are generally preferably used as antiperspirants, particularly inorganic and organic metal salts of the elements aluminium, zinc, magnesium, tin and zircon as well as their mixtures, wherein particularly halogenides such as aluminium chloride, alkaline aluminium hydroxychlorides, zirconyl oxychlorides and zirconyl hydroxychlorides as well as their mixtures are used. Often these aluminium and zirconium salts and mixtures thereof are also used in a complexed form, wherein as complex builders preferably propylene glycol, polyethylene glycol or glycine are used.

The present invention also relates to a method for producing a perfumed product, particularly a perfumed product according to the invention, comprising the following steps:
  i) Providing a compound according to the present invention or a perfume composition according to the present invention,
  ii) providing one or several further components of the perfumed product to be produced, and
  iii) contacting or mixing the further components provided in step ii) with a sensorially effective amount of the components provided in step i).

The present invention also relates to a method of imparting and/or increasing i) floral and/or ii) green and/or iii) lily of the valley odor characteristics to a perfumed product comprising the step of adding thereto a compound according to the invention or a perfume composition according to the invention.

Another problem to be solved by the present invention was to provide novel methods for the production of the compounds according to the present invention.

A method according to the invention for producing the compound according to the present invention comprises the following steps

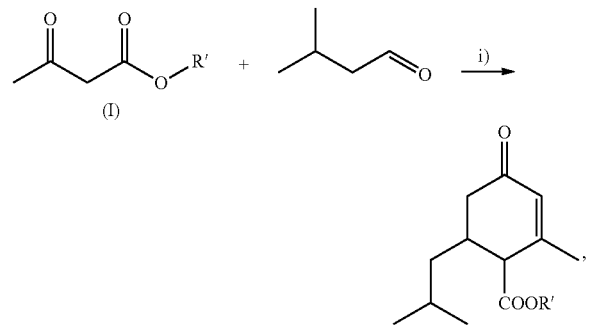

wherein the group R' is alkyl, preferably ethyl, and the reaction takes place in the presence of a base (i), preferably piperidine as base (i).

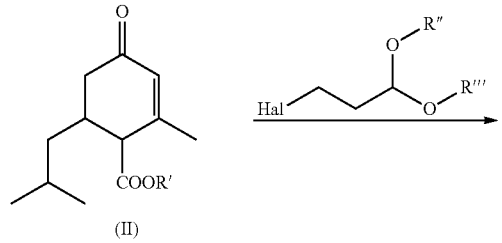

(II)

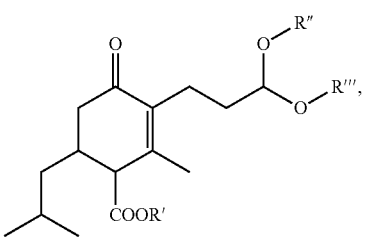

(III)

wherein group R' is alkyl, preferably ethyl, the groups R" and R'" are independently alkyl, preferably methyl or ethyl, or may be connected via an alkyl group, preferably ethane-1,2-diyl or propane-1,2-diyl, to form a ring, and Hal is chlorid, bromid, orjodid, preferably bromid. In a preferred embodiment of this reaction step (II) 3-bromo-1,1-dimethoxypropane is used as a reactant. The product from reaction step (I) can be used as reagent for reaction step (II).

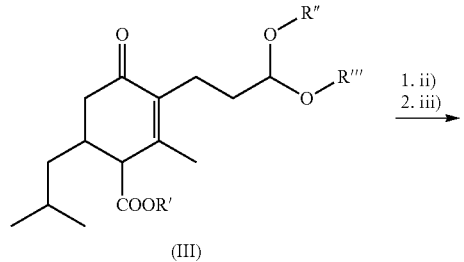

(III)

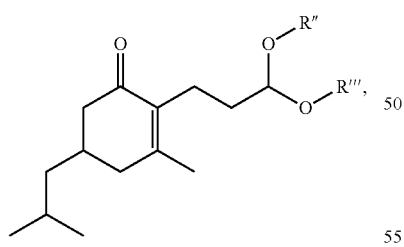

wherein group R' is alkyl, preferably ethyl, and the groups R" and R'" are independently alkyl, preferably methyl or ethyl, or may be connected via an alkyl group, preferably ethane-1,2-diyl or propane-1,2-diyl, to form a ring. Step ii) of this reaction step is a saponification reaction and step iii) of this reaction step is a decarboxylation step. This reaction step (III) is performed in the presence of a base, preferably sodium hydroxide or potassium hydroxide. The product from reaction step (II) can be used as reagent for reaction step (III).

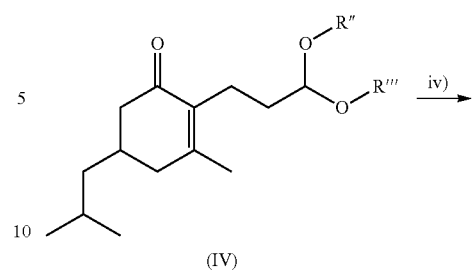

(IV)

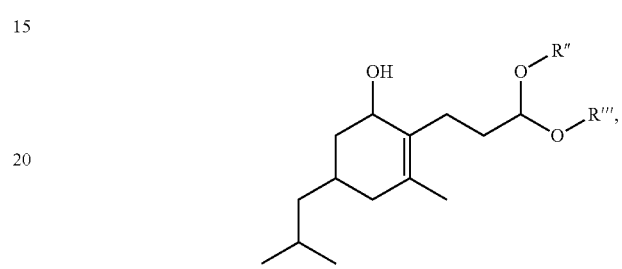

wherein the groups R" and R'" are independently alkyl, preferably methyl or ethyl, or may be connected via an alkyl group, preferably ethane-1,2-diyl or propane-1,2-diyl, to form a ring, and the reaction is performed in the presence of a reducing agent (iv), preferably Lithium aluminium hydride (LAH). The product from reaction step (III) can be used as reagent for reaction step (IV).

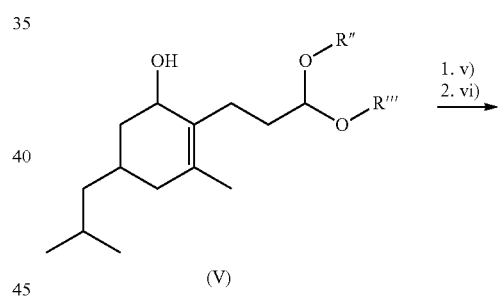

(V)

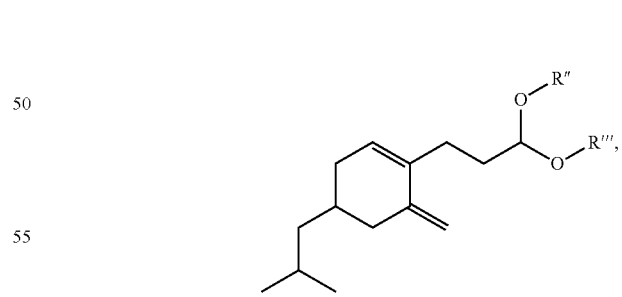

wherein the groups R" and R'" are independently alkyl, preferably methyl or ethyl, or may be connected via an alkyl group, preferably ethane-1,2-diyl or propane-1,2-diyl, to form a ring. Step v) of this reaction step is a mesylation reaction and step vi) of this reaction step is an elimination step. This reaction step (V) is performed in the presence of a base, preferably triethylamine. The product from reaction step (IV) can be used as reagent for reaction step (V).

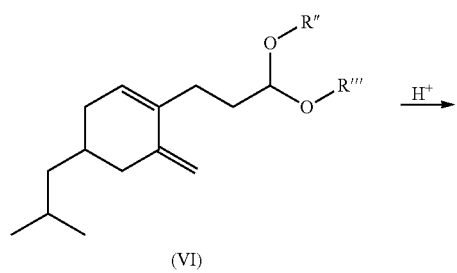

(VI)

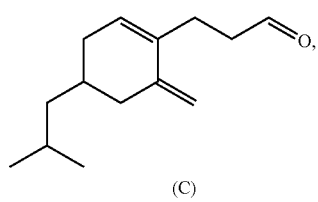

(C)

wherein the groups R" and R'" are independently alkyl, preferably methyl or ethyl, or may be connected via an alkyl group, preferably ethane-1,2-diyl or propane-1,2-diyl, to form a ring. This reaction step (VI) is performed in the presence of an acid, preferably a carboxylic acid, especially formic acid. The product from reaction step (V) can be used as reagent for reaction step (VI).

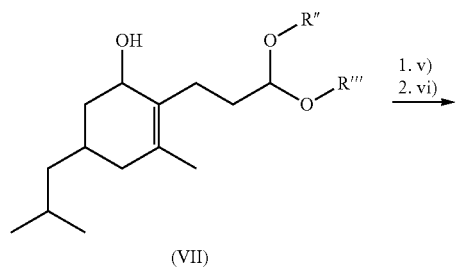

(VII)

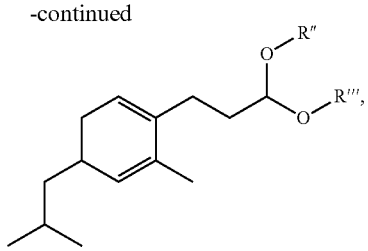

wherein the groups R" and R'" are independently alkyl, preferably methyl or ethyl, or may be connected via an alkyl group, preferably ethane-1,2-diyl or propane-1,2-diyl, to form a ring. Step u) of this reaction step is a mesylation reaction and step vi) of this reaction step is an elimination step. This reaction step (VII) is performed in the presence of a base, preferably triethylamine. The product from reaction step (IV) can be used as reagent for reaction step (VII).

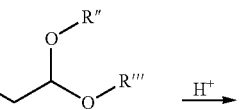

(VIII)

(B)

wherein the groups R" and R'" are independently alkyl, preferably methyl or ethyl, or may be connected via an alkyl group, preferably ethane-1,2-diyl or propane-1,2-diyl, to form a ring. This reaction step (VIII) is performed in the presence of an acid, preferably a carboxylic acid, especially formic acid. The product from reaction step (VII) can be used as reagent for reaction step (VIII).

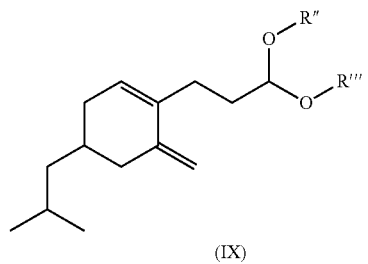

(IX)

and/or

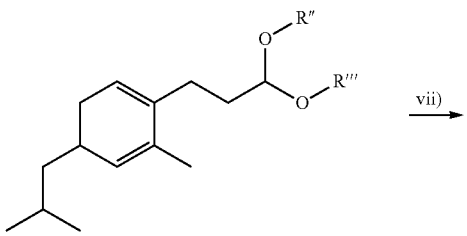

vii)

-continued

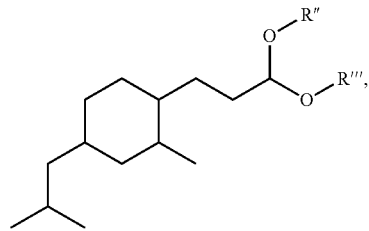

wherein the groups R" and R'" are independently alkyl, preferably methyl or ethyl, or may be connected via an alkyl group, preferably ethane-1,2-diyl or propane-1,2-diyl, to form a ring. This reaction step (VIII) is preferably performed in the presence of Hydrogen (vii) and Palladium on activated carbon as catalyst at high temperature and pressure. The product from reaction step (V), the product from reaction step (VII), or a mixture of the products from reaction step (V) and (VII) can be used as reagent(s) (crude) for reaction step (IX).

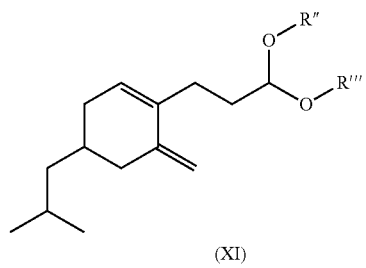

(XI)

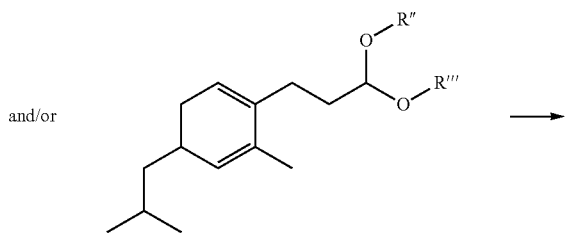

and/or wherein the groups R" and R'" are independently alkyl, preferably methyl or ethyl, or may be connected via an alkyl group, preferably ethane-1,2-diyl or propane-1,2-diyl, to form a ring. This reaction step (X) is performed in the presence of an acid, preferably a carboxylic acid, especially formic acid. The product from reaction step (IX) can be used as reagent for reaction step (X).

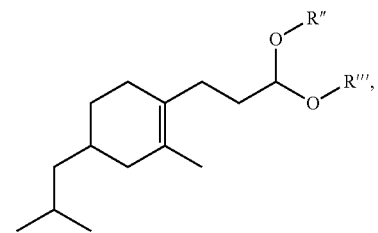

wherein the groups R" and R'" are independently alkyl, preferably methyl or ethyl, or may be connected via an alkyl group, preferably ethane-1,2-diyl or propane-1,2-diyl, to form a ring. This reaction step (VIII) is preferably performed in the presence of Hydrogen (vii) and Palladium on activated carbon as catalyst. The product from reaction step (V), the product from reaction step (VII), or a mixture of the products from reaction step (V) and (VII) can be used as reagent(s) for reaction step (XI).

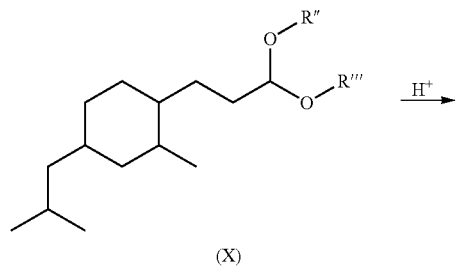

(X)

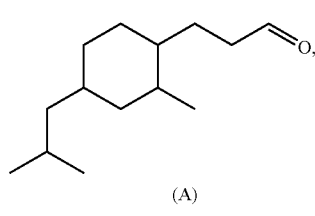

(A)

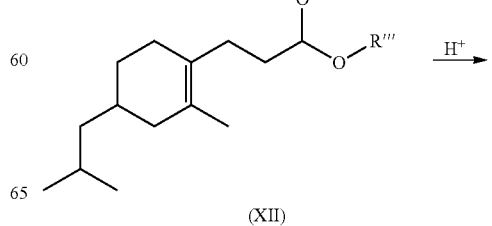

(XII)

-continued

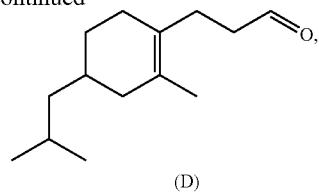

wherein the groups R″ and R‴ are independently alkyl, preferably methyl or ethyl, or may be connected via an alkyl group, preferably ethane-1,2-diyl or propane-1,2-diyl, to form a ring. This reaction step (XII) is performed in the presence of an acid, preferably a carboxylic acid, especially formic acid. The product from reaction step (XI) can be used as reagent for reaction step (XII).

A process for the preparation of a compound according to the invention, comprises at least one, two, three, four, five or six of the above mentioned reactions steps (I), (II), (III), (IV), (V), (VI), (VII), (VIII), (IX), (X), (XI), and (XII).

A process according to the invention for the preparation of 3-(4-isobutyl-2-methyl-cyclohexyl)propanal comprises at least the one, two, three, four, five, six, seven or eight of the above mentioned reactions steps (I), (II), (III), (IV), (V), (VII), (IX), and (X).

A process according to the invention for the preparation of 3-(4-isobutyl-2-methyl-cyclohexyl)propanal preferably comprises at least the above mentioned reaction step (X).

A process according to the invention for the preparation of 3-(4-isobutyl-6-methyl-cyclohexa-1,5-dien-1-yl)propanal comprises at least one, two, three, four, five, or six of the above mentioned reactions steps (I), (II), (III), (IV), (VII), and (VIII).

A process according to the invention for the preparation of 3-(4-isobutyl-6-methyl-cyclohexa-1,5-dien-1-yl)propanal preferably comprises at least the above mentioned reaction step (VIII).

A process according to the invention for the preparation of 3-(4-isobutyl-6-methylene-cyclohexen-1-yl)propanal comprises at least one, two, three, four, five, six, seven or eight of the above mentioned reactions steps (I), (II), (III), (IV), (V), and (VI).

A process according to the invention for the preparation of 3-(4-isobutyl-6-methylene-cyclohexen-1-yl)propanal preferably comprises at least the above mentioned reaction step (VI).

A process according to the invention for the preparation of 3-(4-isobutyl-6-methyl-cyclohexen-1-yl)propanal comprises at least one, two, three, four, five, six, seven or eight of the above mentioned reactions steps (I), (II), (III), (IV), (V), (VII), (XI), and (XII).

A process according to the invention for the preparation of 3-(4-isobutyl-6-methyl-cyclohexen-1-yl)propanal preferably comprises at least the above mentioned reaction step (XII).

In the following, the present invention will be illustrated in more detail by means of selected examples. Unless otherwise stated, all specifications thereby relate to the weight.

EXAMPLES

Example 1: Perfume Composition A

| | Parts by weight | |
|---|---|---|
| Components | perfume composition A1 (comparison) | perfume compositio A2 (according to the invention) |
| ETHYL ACETOACETATE | 4.0 | 4.0 |
| HEXENOL CIS-3 10% DPG | 3.0 | 3.0 |
| HEXENYL ACETATE CIS-3 10% DPG | 3.0 | 3.0 |
| HEXENYL BENZOATE CIS-3 10% DPG | 3.0 | 3.0 |
| VERTOCITRAL 10% DPG | 5.0 | 5.0 |
| CYCLOGALBANAT ® 10% DPG | 3.0 | 3.0 |
| STYRALYL ACETATE 10% DPG | 6.0 | 6.0 |
| BERGAMOT OIL BERGAPTEN FREE FF | 6.0 | 6.0 |
| MANDARIN OIL DIST. DECOL. | 15.0 | 15.0 |
| METHYL ANTHRANILATE 10% DPG | 5.0 | 5.0 |
| RED BERRY EXTR. | 2.0 | 2.0 |
| DECALACTONE GAMMA | 2.0 | 2.0 |
| ALLYL CAPROATE 10% DPG | 5.0 | 5.0 |
| PRUNELLA TYPE BASE | 6.0 | 6.0 |
| HELIONAL | 20.0 | 20.0 |
| MUGETANOL | 10.0 | 10.0 |
| ETHYL LINALOOL | 35.0 | 35.0 |
| CITRONELLOL 950 | 10.0 | 10.0 |
| GERANIOL SUPER | 3.0 | 3.0 |
| ROSAPHEN ® | 8.0 | 8.0 |
| CITRONELLYL ACETATE EXTRA | 2.0 | 2.0 |
| DAMASCONE BETA 10% DPG | 6.0 | 6.0 |
| BENZYL ACETATE | 10.0 | 10.0 |
| HEDION HC/30 | 30.0 | 30.0 |
| HEDIONE | 140.0 | 140.0 |
| HEXYL CINNAMIC ALDEHYDE ALPHA | 30.0 | 30.0 |
| LACTOJASMONE | 3.0 | 3.0 |
| BENZYL SALICYLATE | 80.0 | 80.0 |
| HEXENYL SALICYLATE CIS-3 | 30.0 | 30.0 |
| METHYL IONONE GAMMA COEUR | 3.0 | 3.0 |
| CLOVE BUD OIL | 1.0 | 1.0 |
| VANILLIN | 1.5 | 1.5 |
| COUMARIN | 1.0 | 1.0 |

-continued

|  | Parts by weight | |
|---|---|---|
| Components | perfume composition A1 (comparison) | perfume compositio A2 (according to the invention) |
| AMBERWOOD ® F | 5.0 | 5.0 |
| CASHMERAN | 8.0 | 8.0 |
| CEDRENE | 15.0 | 15.0 |
| ISO E SUPER NON DISCOLORING | 50.0 | 50.0 |
| BRAHMANOL ® | 25.0 | 25.0 |
| SANDALORE | 5.0 | 5.0 |
| AMBROXIDE | 2.0 | 2.0 |
| AMBRETTOLIDE | 5.0 | 5.0 |
| AURELIONE ® | 16.0 | 16.0 |
| GLOBALIDE ® | 24.0 | 24.0 |
| MACROLIDE ® SUPRA | 16.0 | 16.0 |
| INDOLE FF 10% DPG | 5.0 | 5.0 |
| Compound A to D | — | 50.0 |
| DIPROPYLENE GLYCOL | 332.5 | 282.5 |
|  | 1,000.0 | 1,000.0 |

By adding 5 wt. % of a compound A, B, C or D or a mixture of compounds A, B, C or D in perfume composition A2 the floral note is intensified relative to perfume oil A1 (without a compound A, B, C, or D). Furthermore, the compound A, B, C, or D endows the composition with perfume oil A2 more power and fullness than the composition with perfume oil A1; on the whole, addition a compound A, B, C or D or a mixture of compounds A, B, C or D results in an odor impression reminiscent of lily of the valley.

Example 2: Perfume Composition B

|  | Parts by weight | |
|---|---|---|
| Components | perfume composition B1 (comparison) | perfume compositio B2 (according to the invention) |
| NONADIENAL TRANS,CIS-2,6 5% TEC 20% DPG | 2.0 | 2.0 |
| ETHYL ACETOACETATE | 3.0 | 3.0 |
| FARENAL ® 10% DPG | 5.0 | 5.0 |
| VERTOCITRAL | 3.0 | 3.0 |
| CYCLOGALBANAT ® 10% DPG | 2.0 | 2.0 |
| STYRALYL ACETATE | 3.0 | 3.0 |
| MELONAL ® | 0.5 | 0.5 |
| DIHYDRO MYRCENOL | 15.0 | 15.0 |
| LINALYL ACETATE | 20.0 | 20.0 |
| LEMON OIL TERPENES FLAVOR WONF | 8.0 | 8.0 |
| EUCALYPTOL NAT. 10% DPG | 0.5 | 0.5 |
| HEXYL ACETATE | 1.5 | 1.5 |
| ISOAMYL ACETATE 10% DPG | 4.0 | 4.0 |
| PRENYL ACETATE 10% DPG | 4.0 | 4.0 |
| ALDEHYDE C14 SO-CALLED | 2.0 | 2.0 |
| ETHYL METHYL BUTYRATE-2 | 1.0 | 1.0 |
| ALLYL CYCLOHEXYL PROPIONATE | 2.0 | 2.0 |
| ALDEHYDE C16 SO-CALLED | 1.0 | 1.0 |
| FRAGOLANE ® | 0.5 | 0.5 |
| MAJANTOL ® | 25.0 | 25.0 |
| LINALOOL | 40.0 | 40.0 |
| DIMETHYL BENZYL CARBINOL | 10.0 | 10.0 |
| TERPINEOL PURE | 10.0 | 10.0 |
| PHENIRAT ® | 30.0 | 30.0 |
| CITRONELLOL 950 | 15.0 | 15.0 |
| GERANIOL 60 | 10.0 | 10.0 |
| CITRONELLYL ACETATE EXTRA | 2.0 | 2.0 |
| HEDIONE | 90.0 | 90.0 |
| HEXYL CINNAMIC ALDEHYDE ALPHA | 35.0 | 35.0 |
| HEXYL SALICYLATE | 160.0 | 160.0 |
| METHYL OCTIN CARBONATE 10% DPG | 2.0 | 2.0 |
| CALONE 1951 10% DPG | 1.0 | 1.0 |
| GALAXOLIDE 50% IN IPM | 20.0 | 20.0 |
| ANETHOL SUPRA 21.5 CELSIUS | 2.0 | 2.0 |
| AGRUMEX HC | 15.0 | 15.0 |

-continued

|  | Parts by weight | |
|---|---|---|
| Components | perfume composition B1 (comparison) | perfume compositio B2 (according to the invention) |
| ORYCLON SPECIAL | 40.0 | 40.0 |
| Compound A to D | — | 15.0 |
| DIPROPYLENE GLYCOL | 415.0 | 400.0 |
|  | 1,000.0 | 1,000.0 |

By adding 1.5 wt. % of a compound A, B, C or D or a mixture of compounds A, B, C or D in perfume composition B2 the floral and natural note is intensified relative to perfume oil B1 (without a compound A, B, C, or D). Furthermore, the compound A, B, C, or D endows the composition with perfume oil B2 more power and fullness than the composition with perfume oil A1; on the whole, addition a compound A, B, C or D or a mixture of compounds A, B, C or D results in an odor impression reminiscent of lily of the valley.

Example 3: Perfume Compositions C

|  | Parts by weight | |
|---|---|---|
| Components | perfume composition C1 (comparison) | perfume compositio C2 (according to the invention) |
| FARENAL ® | 3.0 | 3.0 |
| FLORAZON | 0.5 | 0.5 |
| HEXENYL ACETATE CIS-3 | 3.0 | 3.0 |
| VERTOCITRAL | 1.0 | 1.0 |
| DYNASCONE 10% DPG | 2.0 | 2.0 |
| CYCLOGALBANAT ® | 2.0 | 2.0 |
| STYRALYL ACETATE | 1.5 | 1.5 |
| DIHYDRO MYRCENOL | 6.0 | 6.0 |
| OXANTHIA 50% IN TEC 10% DPG | 10.0 | 10.0 |
| LEMON OIL ITAL. | 10.0 | 10.0 |
| ORANGE OIL BRASIL | 50.0 | 50.0 |
| HEXYL ACETATE | 2.0 | 2.0 |
| ISOAMYL ACETATE | 0.5 | 0.5 |
| PRENYL ACETATE | 0.5 | 0.5 |
| ETHYL BUTYRATE 10% DPG | 2.0 | 2.0 |
| ALDEHYDE C14 SO-CALLED | 25.0 | 25.0 |
| DECALACTONE GAMMA | 5.0 | 5.0 |
| ETHYL METHYL BUTYRATE-2 | 1.0 | 1.0 |
| ALLYL CAPROATE | 1.5 | 1.5 |
| ALLYL CYCLOHEXYL PROPIONATE | 3.0 | 3.0 |
| ALLYL HEPTOATE | 2.5 | 2.5 |
| MELOZONE | 2.0 | 2.0 |
| CALONE 1951 | 0.5 | 0.5 |
| MUGETANOL | 10.0 | 10.0 |
| LINALOOL | 25.0 | 25.0 |
| DIMETHYL BENZYL CARBINYL ACETATE | 6.0 | 6.0 |
| DIMETHYL BENZYL CARBINYL BUTYRAT | 4.0 | 4.0 |
| PHENYLETHYL ACETATE | 1.5 | 1.5 |
| PHENYLETHYL ALCOHOL | 15.0 | 15.0 |
| CITRONELLOL 950 | 10.0 | 10.0 |
| GERANIOL SUPER | 5.0 | 5.0 |
| GERANYL ACETATE PURE | 15.0 | 15.0 |
| ISODAMASCON ® | 2.0 | 2.0 |
| BENZYL ACETATE | 15.0 | 15.0 |
| HEDIONE | 90.0 | 90.0 |
| HEXYL CINNAMIC ALDEHYDE ALPHA | 35.0 | 35.0 |
| JASMONE CIS | 0.5 | 0.5 |
| BENZYL SALICYLATE | 80.0 | 80.0 |
| HEXENYL SALICYLATE CIS-3 | 30.0 | 30.0 |
| ISORALDEINE 70 | 35.0 | 35.0 |
| HERBAFLORAT | 15.0 | 15.0 |
| ISO E SUPER | 15.0 | 15.0 |
| ISOBORNYL CYCLOHEXANOL | 30.0 | 30.0 |
| BRAHMANOL ® | 10.0 | 10.0 |
| AMBROXIDE | 1.5 | 1.5 |
| GLOBALIDE ® | 5.0 | 5.0 |
| GALAXOLIDE 50% IN DPG | 120.0 | 120.0 |

| Components | Parts by weight | |
|---|---|---|
| | perfume composition C1 (comparison) | perfume compositio C2 (according to the invention) |
| Compound A to D | — | 65.0 |
| DIPROPYLENE GLYCOL | 290.0 | 225.0 |
| | 1,000.0 | 1,000.0 |

By adding 6.5 wt. % of a compound A, B, C or D or a mixture of compounds A, B, C or D in perfume composition C2 the aqueous-fruity character is intensified relative to perfume oil C1 (without a compound A, B, C, or D). Moreover, in the perfume composition C2 with compound A, B, C, or D, the diffusivity is increased relative to the perfume composition C1, without a compound A, B, C or D; on the whole, addition of a compound A, B, C or D results in an odor impression reminiscent of lily of the valley.

Example 4: Synthesis of ethyl-6-isobutyl-2-methyl-4-oxo-cyclohex-2-ene-1-carboxylate 201.4 g (1.54 mol) ethylacetoacetate (CAS Number: 141-97-9) and 53.0 g (0.62 mol) isovaleraldehyde (CAS Number: 590-86-3) were added to a three-necked round bottom flask. 5.2 g piperidine in 35 mL ethanol were added at room temperature to the reaction mixture. The reaction mixture was then stirred for five hours under reflux. Subsequently the reaction mixture was cooled down to room temperature and methyl tert-butyl ether was added. The layers are separated, and the aqueous phases was washed with methyl tert-butyl ether. The organic phases were collected, washed two times with water and dried over sodium sulfate (30 g). The solvent was removed under reduced pressure. Subsequently, the crude product was purified by distillation. Ethyl-6-isobutyl-2-methyl-4-oxo-cyclohex-2-ene-1-carboxylate is obtained as a liquid (138.5 g, 93.8%).

MS: m/z (%)=238, 165, 154, 126, 121, 109, 98, 79, 57, 41, 29.

$^1$H NMR (400 MHz, Chloroform-d) δ 5.97 (d, J=2.6 Hz, 1H), 5.97-5.94 (m, 1H), 4.24 (dtd, J=10.7, 7.3, 3.6 Hz, 2H), 4.20 (dd, J=14.3, 7.2 Hz, 2H), 3.19 (d, J=5.0 Hz, 1H), 3.06 (d, J=6.4 Hz, 1H), 2.66 (dd, J=16.2, 4.6 Hz, 1H), 2.59 (d, J=3.0 Hz, 1H), 2.59-2.48 (m, 1H), 2.43-2.31 (m, 1H), 2.33-2.25 (m, 1H), 2.09 (dd, J=16.5, 8.2 Hz, 1H), 1.98 (d, J=1.3 Hz, 3H), 1.97-1.95 (m, 3H), 1.75 (dp, J=13.5, 6.7 Hz, 1H), 1.69-1.53 (m, 1H), 1.37-1.23 (m, 2H), 1.30 (t, J=7.1 Hz, 3H), 1.28 (t, J=7.2 Hz, 3H), 1.24-1.13 (m, 2H), 0.90 (d, J=6.6 Hz, 3H), 0.90 (d, J=6.6 Hz, 3H), 0.88 (d, J=6.6 Hz, 3H), 0.86 (d, J=6.5 Hz, 3H).

$^{13}$C NMR (101 MHz, CDCl3) δ=199.39, 198.12, 171.86, 170.26, 156.69, 155.72, 128.45, 128.11, 61.31, 61.18, 53.07, 51.01, 42.98, 42.37, 40.37, 39.09, 35.35, 34.79, 24.98, 24.46, 23.38, 23.20, 23.09, 22.61, 22.49, 21.70, 14.31, 14.22.

Example 5: Synthesis of ethyl-3-(3,3-dimethoxy-propyl)-6-isobutyl-2-methyl-4-oxo-cyclohex-2-ene-1-carboxylate 5.5 g (49.0 mmol) Potassium tert-butoxide were added to 100 mL tert-butyl alcohol. 0.2 g Tetrabutylammonium iodide (TBAI) and 10.0 g ethyl-6-isobutyl-2-methyl-4-oxo-cyclohex-2-ene-1-carboxylate (40.8 mmol) were added to the mixture at room temperature. The mixture was stirred at 65° C. for four hours. Subsequently the mixture was let cool down to room temperature and 9.0 g (49.0 mmol) 3-bromo-1,1-dimethoxypropane was added dropwise. Subsequently tert-butoxide was removed under reduced pressure. To the residue methyl tert-butyl ether and water were added. The layers are separated, and the aqueous phases was washed with methyl tert-butyl ether. The organic phases were collected, washed two times with water and dried over sodium sulfate (30 g). The solvent was removed under reduced pressure. Subsequently, the crude product was purified by distillation. Ethyl-3-(3,3-Dimethoxypropyl)-6-isobutyl-2-methyl-4-oxo-cyclohex-2-ene-1-carboxylate is obtained as a liquid (7.5 g, 51.5% %) with a purity of 97%.

MS: m/z (%)=325, 308, 277, 203, 147, 109, 82, 67, 41.

$^1$H NMR (400 MHz, Chloroform-d) δ 4.35 (tt, J=5.7, 1.6 Hz, 2H), 4.26-4.16 (m, 4H), 3.31 (d, J=1.0 Hz, 12H), 3.20 (dd, J=5.5 Hz, 1H), 3.07 (dd, J=11.8, 6.3 Hz, 1H), 2.71-2.60 (m, 1H), 2.49-2.40 (m, 1H), 2.40-2.32 (m, 6H), 2.32 (s, 2H), 2.16-2.07 (m, 2H), 1.97 (s, 3H), 1.94 (d, J=0.8 Hz, 3H), 1.82-1.70 (m, 1H), 1.68-1.56 (m, 5H), 1.31-1.27 (m, 6H), 1.25 (dd, J=7.1, 3.3 Hz, 2H), 1.23-1.10 (m, 2H), 0.95-0.82 (m, 12H).

$^{13}$C NMR (101 MHz, CDCl3) δ 198.32, 197.16, 172.46, 170.86, 150.10, 148.62, 136.72, 136.50, 104.14, 104.12, 61.17, 60.99, 54.49, 52.72, 52.65, 52.59, 42.93, 42.54, 40.71, 39.54, 34.62, 33.88, 31.17, 24.99, 24.37, 23.14, 22.67, 22.51, 21.82, 20.74, 20.69, 20.24, 19.77, 14.33.

Example 6: Synthesis of 2-(3,3-dimethoxypropyl)-5-isobutyl-3-methyl-cyclohex-2-en-1-one 20 g (3.4 mmol) ethyl-3-(3,3-dimethoxypropyl)-6-isobutyl-2-methyl-4-oxo-cyclohex-2-ene-1-carboxylate was mixed with 24 mL methanol. 4 g (50 mmol) sodium hydroxide and 30 g water were added at room temperature. The mixture was stirred for five seven hours under reflux. Subsequently the methanol was removed under reduced pressure. To the residue methyl tert-butyl was added. The layers are separated, and the aqueous phases was washed with methyl tert-butyl ether. The organic phases were collected, washed two times with water and dried over sodium sulfate (30 g). The solvent was removed under reduced pressure. Subsequently, the crude product was purified by distillation. 2-(3,3-Dimethoxypropyl)-5-isobutyl-3-methyl-cyclohex-2-en-1-one is obtained as a liquid (13.2 g, 72.4%) with a purity of 98%.

MS: m/z (%)=253, 236, 221, 205, 191, 75, 71, 41.

$^1$H NMR (400 MHz, Chloroform-d) δ 4.35 (t, J=5.7 Hz, 1H), 3.32 (s, 6H), 2.51-2.44 (m, 1H), 2.32 (dt, J=13.9, 7.2 Hz, 3H), 1.96 (s, 3H), 1.95 (s, 3H), 1.72-1.58 (m, 1H), 1.66-1.58 (m, 2H), 1.20 (t, J=6.7 Hz, 2H), 0.88 (d, J=2.5 Hz, 3H), 0.87 (d, J=2.3 Hz, 3H).

¹³C NMR (101 MHz, CDCl3) δ 198.97, 154.80, 134.65, 104.21, 52.61, 52.56, 45.29, 44.34, 39.79, 31.99, 31.47, 24.62, 22.74, 22.63, 21.16, 20.46.

Example 7: Synthesis of 2-(3,3-dimethoxypropyl)-5-isobutyl-3-methyl-cyclohex-2-en-1-ol 0.38 g (10.0 mmol) lithium aluminium hydride were added to 60 mL THF and cooled down to 5° C. At this temperature 8.04 g (30 mmol) 2-(3,3-Dimethoxypropyl)-5-isobutyl-3-methylcyclohex-2-en-1-one were added carefully. The mixture was stirred at room temperature for three hours. Subsequently the mixture was quenched with water. To the residue methyl tert-butyl was added. The layers are separated, and the aqueous phases was washed with methyl tert-butyl ether. The organic phases were collected, washed two times with water and dried over sodium sulfate (30 g). The solvent was removed under reduced pressure. Subsequently, the crude product was purified by distillation. 2-(3,3-dimethoxypropyl)-5-isobutyl-3-methyl-cyclohex-2-en-1-ol is obtained as a liquid (8.0 g, 98.8%) with a purity of 98%.

MS: m/z (%)=238, 223, 206, 167, 149, 123, 105, 75, 41.
¹H NMR (600 MHz, Benzene-d6) δ 4.44 (t, J=5.7 Hz, 1H), 4.11 (q, J=6.5 Hz, 1H), 3.20 (s, 3H), 3.19 (s, 3H), 2.51 (ddd, J=14.8, 9.6, 6.3 Hz, 1H), 2.34 (ddd, J=13.5, 9.4, 6.8 Hz, 1H), 1.98-1.88 (m, 3H), 1.78 (q, J=11.1, 10.5 Hz, 1H), 1.60 (d, J=1.7 Hz, 3H), 1.59-1.51 (m, 3H), 1.26 (d, J=6.5 Hz, 1H), 1.09-1.00 (m, 3H), 0.85 (d, J=6.6 Hz, 3H), 0.84 (d, J=6.5 Hz, 3H).
¹³C NMR (151 MHz, C6D6) δ 133.86, 129.07, 104.57, 70.08, 52.28, 51.87, 46.49, 40.94, 39.79, 31.89, 30.48, 24.94, 23.55, 23.16, 22.80, 19.34.

Example 8: Synthesis of 1-(3,3-dimethoxypropyl)-4-isobutyl-6-methylene-cyclohexene and 2-(3,3-Dimethoxypropyl)-5-isobutyl-3-methyl-cyclohexa-1,3-diene 6.0 g (22.2 mmol) 2-(3,3-Dimethoxypropyl)-5-isobutyl-3-methyl-cyclohex-2-en-1-ol were dissolved in 60 mL toluene and 360 mg 4-dimethylaminopyridine (DMAP) and 18 g (0.18 mol) triethylamine were added at room temperature. The mixture was cooled down to 0 to 5° C. and 4.8 g (44.4 mmol) methanesulfonyl chloride were added dropwise at this temperature. The mixture was stirred for at least 12 hours at room temperature and subsequently for two hours under reflux. Subsequently the mixture was cooled down to 0 to 5° C. and 50 mL water was added to the mixture and the mixture was stirred for 1 hour. The phases were separated and the aqueous phase was extracted with toluene twice. The organic phases were collected, washed with water and dried over sodium sulfate (30 g). The solvent was removed under reduced pressure. Subsequently, the crude product was purified by column chromatography. 4.8 g of 1-(3,3-dimethoxypropyl)-4-isobutyl-6-methylenecyclohexene and 2-(3,3-Dimethoxypropyl)-5-isobutyl-3-methyl-cyclohexa-1,3-diene were obtained as mixture.

1-(3,3-Dimethoxypropyl)-4-isobutyl-6-methylene-cyclohexene:
MS: m/z (%)=252, 220, 175, 131, 119, 105, 88, 75, 58, 41.
¹H NMR (600 MHz, Benzene-d6) δ 5.65-5.60 (m, 1H), 5.13-5.09 (m, 1H), 4.87-4.84 (m, 1H), 4.39 (t, J=5.6 Hz, 1H), 3.17 (s, 3H), 3.16 (s, 3H), 2.46-2.39 (m, 2H), 2.39 (ddd, J=14.9, 3.0, 1.3 Hz, 1H), 2.08 (dt, J=17.7, 4.8 Hz, 1H), 2.00 (ddt, J=13.6, 11.3, 2.0 Hz, 1H), 1.94 (ddt, J=9.6, 6.6, 5.6 Hz, 2H), 1.80-1.72 (m, 1H), 1.65 (ddhept, J=17.8, 9.5, 1.4 Hz, 1H), 1.61-1.53 (m, J=6.7 Hz, 1H), 1.08 (dt, J=14.1, 7.1 Hz, 1H), 1.03 (dt, J=13.5, 7.2 Hz, 1H), 0.83 (d, J=6.8 Hz, 3H), 0.82 (d, J=6.8 Hz, 3H).
¹³C NMR (151 MHz, Benzene-d6) δ 143.66, 136.75, 127.22, 108.32, 104.49, 52.23, 52.65, 45.72, 39.83, 33.39, 32.34, 32.21, 28.26, 25.07, 23.11, 22.81.

2-(3,3-Dimethoxypropyl)-5-isobutyl-3-methyl-cyclohexa-1,3-diene
¹H NMR (400 MHz, Benzene-d6) δ 5.56 (t, J=4.7 Hz, 1H), 5.52-5.48 (m, 1H), 3.17 (s, 3H), 3.16 (s, 3H), 2.29-2.21 (m, 3H), 2.04-1.97 (m, 1H), 1.87-1.80 (m, 3H), 1.78 (t, J=1.8 Hz, 3H), 1.77-1.68 (m, 1H), 1.60-1.53 (m, 1H), 1.40-1.17 (m, 2H), 0.85 (d, J=6.6 Hz, 3H), 0.84 (d, J=6.5 Hz, 3H).
¹³C NMR (101 MHz, Benzene-d6) δ 137.67, 132.83, 128.98, 121.20, 104.27, 52.25, 52.20, 44.12, 32.44, 31.59, 30.04, 28.18, 25.31, 22.97, 22.84, 19.72.

Example 9: Synthesis of 3-(4-isobutyl-6-methyl-cyclohexa-1,5-dien-1-yl)propanal and 3-(4-isobutyl-6-methylenecyclohexen-1-yl)propanal (B+C)

1 g of a mixture of 1-(3,3-dimethoxypropyl)-4-isobutyl-6-methylene-cyclohexene and 2-(3,3-Dimethoxypropyl)-5-isobutyl-3-methyl-cyclohexa-1,3-diene were mixed with 1.2 g formic acid and stirred for 1.5 hours at room temperature. Subsequently the mixture was added to sodium bicarbonate (NaHCO₃). The organic phases were separated, washed two times with water, dried over sodium sulfate and the solvent was removed under reduced pressure. Subsequently, the crude product was purified by column chromatography. 0.7 g of 3-(4-isobutyl-6-methyl-cyclohexa-1,5-dien-1-yl)propanal and 3-(4-isobutyl-6-methylenecyclohexen-1-yl)propanal were obtained as mixture with a purity of 93%. Both aldehydes can be separated by preparative GC.

3-(4-Isobutyl-6-methyl-cyclohexa-1,5-dien-1-yl)propanal (B):
Odor: Floral, Green, Lily of the valley.
MS: m/z (%)=206, 131, 119, 105, 91, 79, 41.
¹H NMR (600 MHz, Benzene-d6) δ 9.32 (t, J=1.6 Hz, 1H), 5.46 (p, J=3.6, 1.8 Hz, 1H), 5.33 (t, J=4.7 Hz, 1H), 2.21 (ddddd, J=9.7, 7.6, 5.8, 4.1, 2.1 Hz, 1H), 2.17 (tq, J=7.7, 1.7 Hz, 2H), 2.08-2.02 (m, 1H), 2.01-1.97 (m, 2H), 1.80-1.72 (m, 1H), 1.62 (t, J=1.9 Hz, 3H), 1.64-1.56 (m, J=6.7 Hz, 1H), 1.26 (dt, J=13.3, 7.4 Hz, 1H), 1.12 (dt, J=13.3, 7.4 Hz, 1H), 0.85 (d, J=6.6 Hz, 3H), 0.83 (d, J=6.6 Hz, 3H).
¹³C NMR (151 MHz, Benzene-d6) δ 200.29, 136.39, 132.25, 129.23, 121.40, 43.98, 42.66, 31.41, 29.85, 25.29, 25.15, 22.92, 22.82, 19.56.

3-(4-Isobutyl-6-methylene-cyclohexen-1-yl)propanal (C):
Odor: Floral, Green, Lily of the valley.
MS: m/z (%)=206, 188, 164, 149, 131, 121, 105, 91, 79, 41.
¹³C NMR (151 MHz, Benzene-d6) δ 200.41, 143.27, 135.44, 127.74, 108.27, 45.59, 42.76, 39.60, 33.21, 32.17, 25.21, 25.05, 23.07, 22.79.
¹H NMR (600 MHz, Benzene-d6) δ 9.33 (t, J=1.6 Hz, 1H), 5.45-5.40 (m, 1H), 4.85-4.80 (m, 1H), 4.78-4.73 (m, 2H), 2.41-2.33 (m, 1H), 2.35-2.29 (m, 1H), 2.14-2.09 (m, 2H), 2.01 (dt, J=17.9, 5.0 Hz, 1H), 1.92 (ddt, J=13.5, 11.2, 2.0 Hz, 1H), 1.73-1.64 (m, 1H), 1.63-1.55 (m, 1H), 1.60-1.49 (m, J=6.9 Hz, 1H), 1.04 (dt, J=14.1, 7.1 Hz, 1H), 0.99 (dt, J=13.5, 7.2 Hz, 1H), 0.81 (d, J=7.0 Hz, 6H).

Example 10: Synthesis of 3-(4-isobutyl-2-methyl-cyclohexyl)propanal (A)

1.1 g (2.15 mmol) of a mixture of 1-(3,3-dimethoxypropyl)-4-isobutyl-6-methylene-cyclohexene and 2-(3,3-Dimethoxypropyl)-5-isobutyl-3-methyl-cyclohexa-1,3-diene were mixed with 2 ml cyclohexane. 80 mg of palladium on activated charcoal were added. The mixture was hydrogenated with hydrogen at 100-190° C. for 8 h at a pressure of 20-25 bar. The catalyst was filtered off. 1.0 g 1-(3,3-dimethoxypropyl)-4-isobutyl-2-methylcyclohexane was obtained with a purity of 95%.

1 g 1-(3,3-dimethoxypropyl)-4-isobutyl-2-methylcyclohexane were mixed with 1.2 g formic acid and stirred for 1.5 hours at room temperature. Subsequently the mixture was added to sodium bicarbonate (NaHCO$_3$). The organic phases were separated, washed two times with water, dried over sodium sulfate and the solvent was removed under reduced pressure. Subsequently, the crude product was purified by column chromatography. 0.7 g of 3-(4-isobutyl-2-methyl-cyclohexyl)propanal (A) were obtained with a purity of 94%.

Odor: Floral, Green, Lily of the valley, Sweet.

MS: m/z (%)=210, 192, 166, 151, 135, 109, 95, 81, 67, 55, 41, 29.

$^1$H NMR (400 MHz, Benzene-d6) δ 9.38 (t, J=1.7 Hz, 1H), 1.96-1.75 (m, 3H), 1.70-1.58 (m, 2H), 1.52-1.43 (m, 2H), 1.40-1.18 (m, 5H), 1.06-0.97 (m, 3H), 0.89 (d, J=6.6 Hz, 6H), 0.80 (d, J=7.0 Hz, 3H), 0.69-0.56 (m, 1H).

$^{13}$C NMR (101 MHz, C$_6$D$_6$) δ 200.94, 47.34, 42.62, 38.36, 36.48, 35.77, 35.71, 29.22, 27.03, 24.95, 23.11, 23.08, 20.10, 17.00.

Example 11: Synthesis of 1-(3,3-dimethoxypropyl)-4-isobutyl-2-methyl-cyclohexene 1.1 g (4.36 mmol) of a mixture of 1-(3,3-dimethoxypropyl)-4-isobutyl-6-methylene-cyclohexene and 2-(3,3-Dimethoxypropyl)-5-isobutyl-3-methyl-cyclohexa-1,3-diene were mixed with 2 ml cyclohexane. 20 mg of palladium on activated charcoal were added. The mixture was hydrogenated with hydrogen at 50° C. for 5 h at a pressure of 2 bar. The catalyst was filtered off. 1.0 g 1-(3,3-dimethoxypropyl)-4-isobutyl-2-methyl-cyclohexene was obtained with a purity of 95%.

MS: m/z (%)=222, 207, 190, 133, 107, 93, 79, 75, 67, 55, 41.

$^1$H NMR (400 MHz, CDCl3) δ 4.32 (t, J=5.7 Hz, 1H), 3.32 (s, 6H), 2.03 (ddt, J=12.0, 7.2, 3.9 Hz, 2H), 1.99-1.89 (m, 2H), 1.76-1.63 (m, 5H), 1.60 (s, 3H), 1.60-1.47 (m, 2H), 1.17-1.06 (m, 3H), 0.87 (d, J=6.6 Hz, 6H).

$^{13}$C NMR (101 MHz, CDCl3) δ 128.82 (C-4), 126.20 (C-5), 104.25 (C-10), 52.49 (C-12), 52.47 (C-14), 46.27 (C-15), 39.02 (C-6), 31.73 (C-1), 30.80 (C-9), 29.98 (C-2), 29.60 (C8), 28.09 (C-3), 24.88 (C-16), 23.10 (C-17), 22.75 (C-18), 18.96 (C-7).

Example 12: Synthesis of 3-(4-isobutyl-6-methyl-cyclohexen-1-yl)propanal (D)

1 g 1-(3,3-dimethoxypropyl)-4-isobutyl-2-methyl-cyclohexene were mixed with 1.2 g formic acid and stirred for 1.5 hours at room temperature. Subsequently the mixture was added to sodium bicarbonate (NaHCO$_3$). The organic phases were separated, washed two times with water, dried over sodium sulfate and the solvent was removed under reduced pressure. Subsequently, the crude product was purified by column chromatography. 0.7 g of 3-(4-isobutyl-6-methyl-cyclohexen-1-yl)propanal (D) were obtained with a purity of 93%.

Odor: Floral, Sweet, Lily of the valley, Creamy.

MS: m/z (%)=208, 190, 165, 151, 133, 107, 81, 67, 55, 41, 29.

$^1$H NMR (600 MHz, Benzene-d6) δ 9.37 (t, J=1.8 Hz, 1H), 2.12 (dd, J=7.4, 2.8 Hz, 2H), 2.00-1.96 (m, 2H), 1.84-1.79 (m, 1H), 1.75-1.70 (m, 1H), 1.65-1.58 (m, 2H), 1.54-1.49 (m, 2H), 1.48 (t, J=1.9 Hz, 3H), 1.41-1.33 (m, 1H), 1.07-1.02 (m, 3H), 0.88 (d, J=2.5 Hz, 3H), 0.87 (d, J=2.6 Hz, 3H).

$^{13}$C NMR (151 MHz, Benzene-d6) δ 200.66, 128.32, 126.84, 46.52, 42.52, 39.22, 31.92, 30.16, 29.60, 25.85, 25.15, 23.26, 22.89, 19.06.

The invention claimed is:

1. A compound selected from the group consisting of:

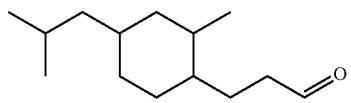

3-(4-isobutyl-2-methyl-cyclohexyl)propanal,

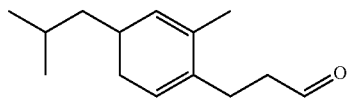

3-(4-isobutyl-6-methyl-cyclohexa-1,5-dien-1-yl)propanal, and

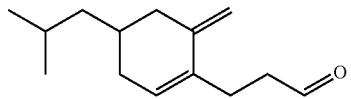

3-(4-isobutyl-6-methylene-cyclohexen-1-yl)propanal.

2. The compound of claim 1, wherein the compound is:

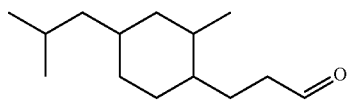

3-(4-isobutyl-2-methyl-cyclohexyl)propanal.

3. The compound of claim 1, wherein the compound is:

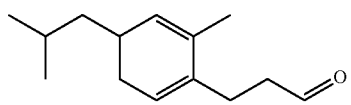

3-(4-isobutyl-6-methyl-cyclohexa-1,5-dien-1-yl)propanal.

4. The compound of claim 1, wherein the compound is:

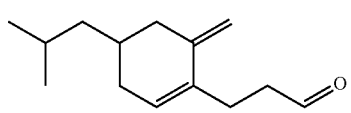

3-(4-isobutyl-6-methylene-cyclohexen-1-yl)propanal.

5. A perfume composition comprising one or more compounds of claim 1 and one or more fragrance ingredients, and optionally, 3-(4-isobutyl-2-methylcyclohex-1-en-1-yl)propanal.

6. A perfumed product comprising the perfume composition of claim 5.

7. The perfumed product of claim 6, wherein the perfumed product is selected from perfume extraits, eau de perfumes, eau de toilettes, aftershaves, eau de colognes, pre-shave products, splash colognes, perfumed refreshing tissues, detergents, textile fresheners, ironing aids, liquid detergents, powdery detergents, laundry pretreatment agents, fabric softeners, laundry soaps, laundry tablets, disinfectants, air fresheners, aerosol sprays, waxes, polishes, personal care agents, hand creams, hand lotions, foot creams, foot lotions, depilatory creams, depilatory lotions, aftershave creams, aftershave lotions, tanning creams, tanning lotions, hair care products, deodorants, antiperspirants, decorative cosmetics, candles, lamp oils, incense sticks, insecticides, repellents, and fuels.

8. A method for imparting a fragrance to a composition comprising adding one or more compounds of claim 1 to the composition.

9. The method of claim 8, wherein the fragrance has a floral odor characteristic, a green odor characteristic, a lily of the valley odor characteristic, or a combination thereof.

10. The method of claim 9, wherein the fragrance additionally has a sweet odor characteristic, a creamy odor characteristic, or a combination thereof.

11. The method of claim 8, wherein the compound is:

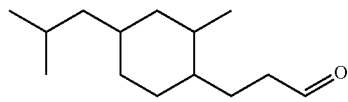

3-(4-isobutyl-2-methyl-cyclohexyl)propanal.

12. The method of claim 8, wherein the compound is:

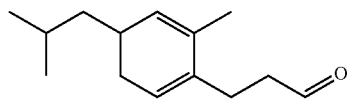

3-(4-isobutyl-6-methyl-cyclohexa-1,5-dien-1-yl)propanal.

13. The method of claim 8, wherein the compound is:

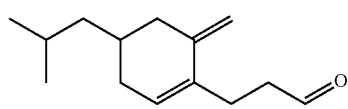

3-(4-isobutyl-6-methylene-cyclohexen-1-yl)propanal.

14. A method for imparting or increasing a fragrance to a product to obtain a perfumed product, the method comprising adding a sensorially effective amount of the perfume composition of claim 5 to the product and obtaining the perfumed product.

15. The method of claim 14, wherein the fragrance has a floral odor characteristic, a green odor characteristic, a lily of the valley odor characteristic, or a combination thereof.

16. The method of claim 14, wherein the perfumed product is selected from perfume extraits, eau de perfumes, eau de toilettes, aftershaves, eau de colognes, pre-shave products, splash colognes, perfumed refreshing tissues, detergents, textile fresheners, ironing aids, liquid detergents, powdery detergents, laundry pretreatment agents, fabric softeners, laundry soaps, laundry tablets, disinfectants, air fresheners, aerosol sprays, waxes, polishes, personal care agents, hand creams, hand lotions, foot creams, foot lotions, depilatory creams, depilatory lotions, aftershave creams, aftershave lotions, tanning creams, tanning lotions, hair care products, deodorants, antiperspirants, decorative cosmetics, candles, lamp oils, incense sticks, insecticides, repellents, and fuels.

17. A method for producing a perfumed product comprising:
(i) providing one or more compounds of claim 1;
(ii) providing one or more additional components of the perfumed product; and
(iii) contacting or mixing the one or more additional components of the perfumed product with a sensorially effective amount of the one or more compounds.

18. A process for preparing a compound of claim 1 comprising one or more of reaction steps (i)-(xii):

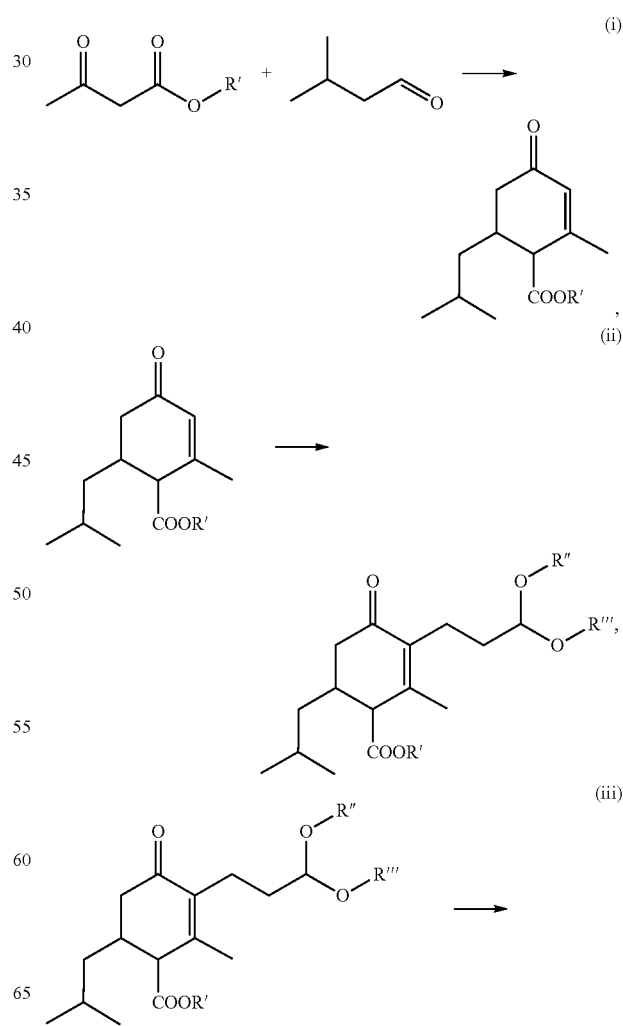

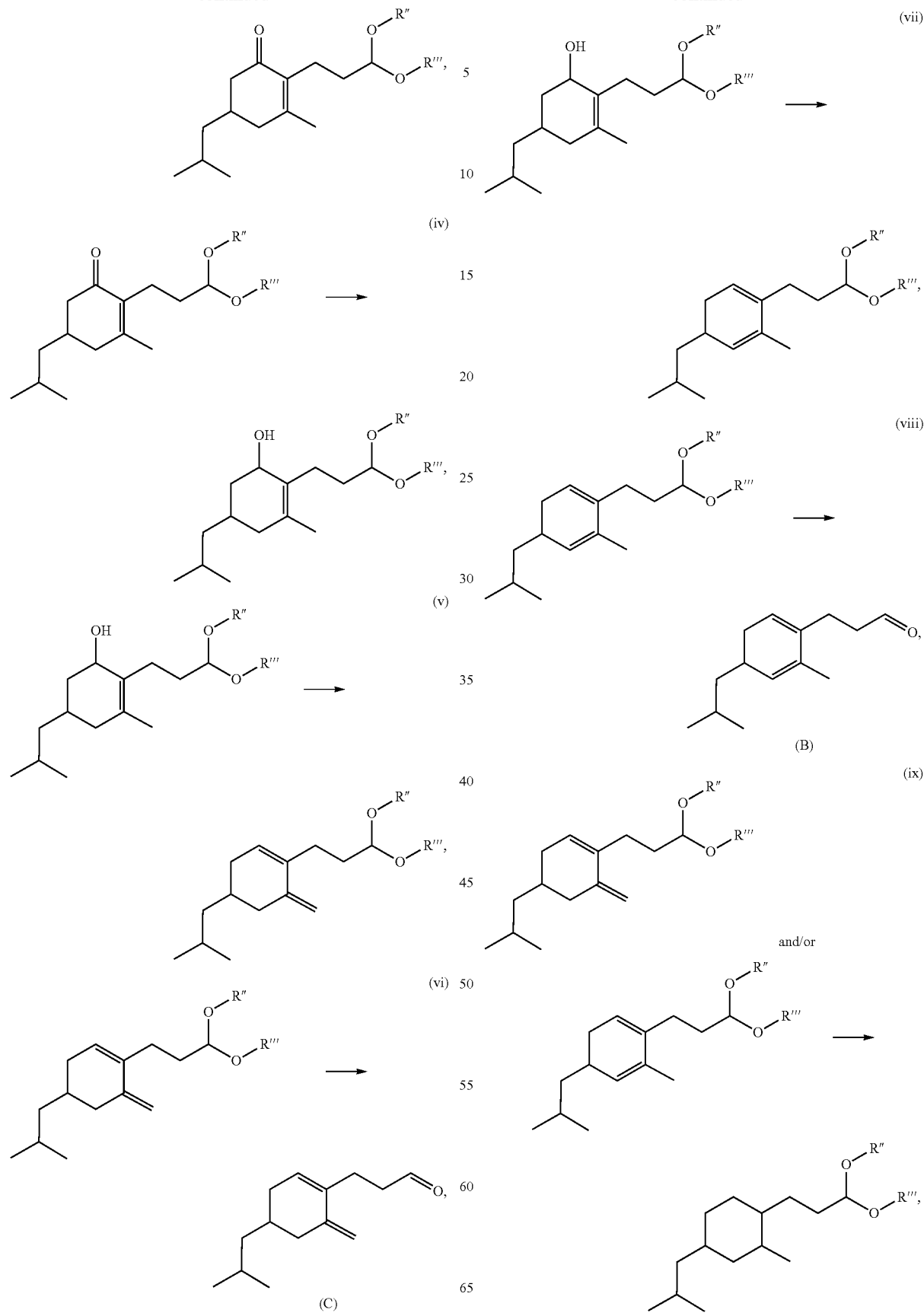

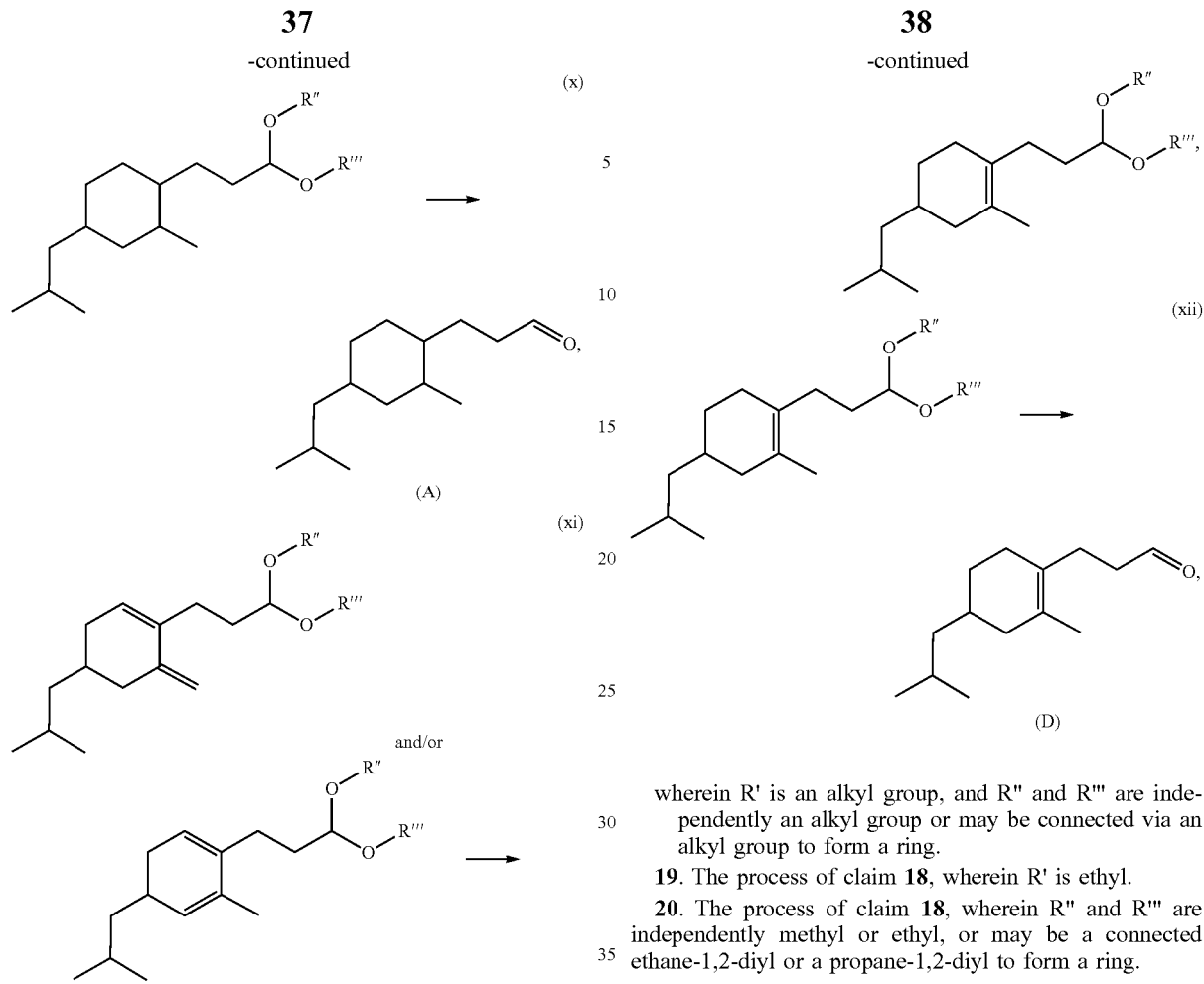
wherein R' is an alkyl group, and R" and R'" are independently an alkyl group or may be connected via an alkyl group to form a ring.
19. The process of claim 18, wherein R' is ethyl.
20. The process of claim 18, wherein R" and R'" are independently methyl or ethyl, or may be a connected ethane-1,2-diyl or a propane-1,2-diyl to form a ring.
* * * * *